United States Patent
Ting et al.

(10) Patent No.: US 9,448,291 B2
(45) Date of Patent: Sep. 20, 2016

(54) HIGH PRESSURE SAMPLE CONTAINMENT SYSTEM FOR ELECTROMAGNETIC MEASUREMENTS

(71) Applicant: Pressure BioSciences, Inc., South Easton, MA (US)

(72) Inventors: Edmund Y. Ting, Kent, WA (US); Alexander Lazarev, Lexington, MA (US)

(73) Assignee: Pressure BioSciences, Inc., South Easton, MA (US)

( * ) Notice: Subject to any disclaimer, the term of this patent is extended or adjusted under 35 U.S.C. 154(b) by 26 days.

(21) Appl. No.: 14/349,518

(22) PCT Filed: Oct. 4, 2012

(86) PCT No.: PCT/US2012/058792
§ 371 (c)(1),
(2) Date: Apr. 3, 2014

(87) PCT Pub. No.: WO2013/052696
PCT Pub. Date: Apr. 11, 2013

(65) Prior Publication Data
US 2015/0002153 A1    Jan. 1, 2015

Related U.S. Application Data

(60) Provisional application No. 61/543,244, filed on Oct. 4, 2011.

(51) Int. Cl.
*G01R 33/30* (2006.01)
*G01N 24/10* (2006.01)
*G01R 33/60* (2006.01)

(52) U.S. Cl.
CPC ............ *G01R 33/305* (2013.01); *G01N 24/10* (2013.01); *G01R 33/60* (2013.01)

(58) Field of Classification Search
CPC ..... G01R 33/305; G01R 33/60; G01N 24/10
See application file for complete search history.

(56) References Cited

U.S. PATENT DOCUMENTS

| | | | | |
|---|---|---|---|---|
| 4,088,944 A | * | 5/1978 | Engler et al. ................. | 324/321 |
| 4,164,700 A | * | 8/1979 | Christoe et al. ............. | 324/318 |
| 4,511,841 A | * | 4/1985 | Bartuska et al. ............. | 324/321 |
| 4,739,270 A | * | 4/1988 | Daugaard et al. ............ | 324/321 |
| 4,923,830 A | * | 5/1990 | Everhart et al. .............. | 501/103 |
| 4,940,942 A | * | 7/1990 | Bartuska et al. ............. | 324/321 |
| 5,202,633 A | * | 4/1993 | Doty et al. ................... | 324/321 |
| 5,313,162 A | * | 5/1994 | De Graaf et al. ............ | 324/307 |
| 5,333,994 A | * | 8/1994 | Doty et al. ................... | 415/202 |
| 5,373,684 A | * | 12/1994 | Vacca ............................ | 53/425 |
| 5,469,061 A | * | 11/1995 | Linehan et al. ............. | 324/321 |
| 5,530,353 A | * | 6/1996 | Blanz ........................... | 324/315 |

(Continued)

OTHER PUBLICATIONS

Yamada et al Pressure-resisting cell for high-pressure, high-resolution nuclear magnetic resonance measurements at very high magnetic fields (Review of Scientific Instruments 72, 1463 (2001).*

*Primary Examiner* — Jermele M Hollington
*Assistant Examiner* — Suresh K Rajaputra
(74) *Attorney, Agent, or Firm* — Lando & Anastasi, LLP (57) ABSTRACT

The present invention is related to systems and methods for chemical and biological analysis and, in particular, to systems, apparatus, and methods of sample conditioning and analysis.

11 Claims, 6 Drawing Sheets

(56) References Cited

U.S. PATENT DOCUMENTS

| | | | |
|---|---|---|---|
| 5,545,998 A * | 8/1996 | Favre et al. | 324/321 |
| 5,705,777 A | 1/1998 | Flanigan et al. | |
| 5,726,570 A * | 3/1998 | Spraul et al. | 324/321 |
| 6,362,624 B1 * | 3/2002 | Wand et al. | 324/321 |
| 6,396,274 B1 * | 5/2002 | Commens et al. | 324/321 |
| 6,507,191 B1 * | 1/2003 | Eguchi et al. | 324/318 |
| 6,972,568 B2 * | 12/2005 | Haner et al. | 324/321 |
| 7,137,474 B2 * | 11/2006 | Yokote | 180/314 |
| 7,247,588 B2 * | 7/2007 | Kwon et al. | 501/105 |
| 8,096,441 B2 * | 1/2012 | Sato et al. | 220/582 |
| 8,448,808 B2 * | 5/2013 | Tani et al. | 220/592 |
| 8,791,695 B2 * | 7/2014 | Balcom et al. | 324/307 |
| 2002/0086153 A1 * | 7/2002 | O'Donnell et al. | 428/336 |
| 2009/0071930 A1 * | 3/2009 | Sato et al. | 215/380 |

* cited by examiner

HIGH PRESSURE SAMPLE CONTAINMENT SYSTEM FOR ELECTROMAGNETIC MEASUREMENTS

This application is a U.S. National Stage Application under 35 U.S.C. §371 of PCT Application Serial No. PCT/US2012/058792 filed on Oct. 4, 2012, which claims the benefit of priority to U.S. Provisional Patent Application Ser. No. 61/543,244 filed on Oct. 4, 2011, the entire disclosures of which are hereby incorporated herein by reference in their entireties for all purposes.

PRIORITY CLAIM

This application claims priority from U.S. Ser. No. 61/543,244, filed Oct. 4, 2011, which is incorporated herein by reference in its entirety.

BACKGROUND OF INVENTION

1. Field of Invention

The present invention is related to systems and methods for chemical and biological analysis and, in particular, to systems, apparatus, and methods of sample conditioning and analysis involving subjecting samples to constant or alternating high hydrostatic pressure in the presence of an electromagnetic fields in order to monitor sample response by means of induced radio frequency electromagnetic signals in the MHz to GHz range.

2. Discussion of Related Art

Magnetic resonance spectroscopy allows understanding of molecular structure and interactions. Electron Paramagnetic Resonance spectroscopy (EPR), alternatively called Electron Spin Resonance spectroscopy (ESR), is playing a unique role in the investigation of chemical and biological sciences. EPR is a technique that is applicable to systems in a paramagnetic state or which can be placed in such a state. Examples:
 1. Free radicals in the solid, liquid or gas phases.
 2. Transition ions including actinide or lanthanide ions.
 3. Various point defects (e.g., An electron trapped at a negative ion vacancy in crystals and glasses or deficiency of an electron, i.e., a positive hole).
 4. Systems with more than one unpaired electron (e.g., Triplet-state systems, biradicals, etc.).
 5. Systems with conducting electrons (e.g., semiconductors, metals).

Therefore, sample containers suitable for EPR must not contribute significantly to the paramagnetic properties of the sample, thus limiting the choices for materials used to make said containers from. For example, metal containers of any kind are unacceptable for EPR spectroscopy. On the other hand, materials typically used to sustain high levels of hydrostatic pressure (e.g. metals) are likely to possess strong paramagnetic or ferromagnetic properties, incompatible with EPR.

Furthermore, it is desirable to separate the liquid sample from the pressure media fluid. If a sample filled cell is directly connected with the fluid in the high pressure generator, the two fluids can mix and confuse the measurement. Thus only direct pressure communication is desirable but not direct fluid communication.

Wand et al. (U.S. Pat. No. 6,362,624B1) teaches that a NMR cells made from "zirconium oxide" or "quartz" that holds samples under modest pressure. Wand shows a maximum pressure of 14,000 psi and he does not show the dimensions needed to achieve and sustain such pressures. This application shows that containers manufactured from ordinary zirconium oxide material are incapable of holding pressure in excess of 40,000 psi. Furthermore, the mounting method taught by Wand will release the full energy content of the pressurization system into the test chamber if the sample containing tube breaks. The release of a large amount of high pressure energy due to sample tube failure could damage the sensitive instrument in which the sample is positioned.

SUMMARY OF THE INVENTION

In one aspect, the present invention provides a system of sample conditioning and analysis as described herein that can achieve pressures in excess of 40,000 psi. Also provided herein is a method of mounting such tubes to minimize energy release if a failure occurs.

In another aspect, the present invention is directed to a sample containing system comprising: a non-metallic sample containing device for measurement of magnetically induced RF signals composing of a inner sample container combined with an outer cover which imposes a compressive stress over the sample container thus allowing the sample container to reach operating pressures greater than 30,000 psi that would normally burst the sample container.

In some embodiments, compressive stress is applied by the use of taper angles on the outside of the sample container and the inside of the outer cover, along with a method of forcing these two components together. In some embodiments, compressive stress is generated by the use of a press interference fit of an outer cover onto the sample container with or without the use of a initial differential temperature. In some embodiments, the material of construction of the sample container is hot isostatically pressed (HIP) transformation toughened zirconia (TTZ) or partially stabilized zirconia (PSZ) (e.g., yttria stabilized (YSZ)), and the outer cover is constructed from high strength engineering materials such as TTZ, PSZ, glass filled PEEK, Macor™, quartz, or other non-RF interfering materials.

In another aspect, the present invention is directed to a sample container made from hot isostatically treated transformation toughened zirconia with an OD to ID ratio of less than 5 and greater than 2.

In some embodiments, the container length to ID ratio is from 50 to 100.

In some embodiments, the sample containing device is mounted to a nonmagnetic base with volume limiting isolation chamber where the sample and pressure source fluids are in pressure communication but not in fluid communication and the volume limited so as to limit contamination of the measurement equipment should the sample container break.

Another aspect of the disclosure is directed to a sample containing system comprising a non-metallic sample container for measurement of magnetically induced RF signals composing of a inner sample receptacle, and a mounting system configured to be secured to the sample container. The mounting system includes a body having a channel formed therein in fluid communication with the sample container when securing the sample container to the mounting system. The sample containing system further comprises an outer cover configured to secure the sample container to the mounting system. The cover imposes a compressive stress over the sample container thus allowing the sample container to reach operating pressures greater than 30,000 psi that would normally burst the sample container.

Embodiments of the sample containing system further may include screw fasteners configured to secure the outer cover to the mounting system. The compressive stress is applied to the sample container by configuring the outside of the sample container and an inside of the outer cover with mating taper angles. The compressive stress may be generated by the use of a press interference fit of the outer cover onto the sample container with or without the use of an initial differential temperature. The material used to construct the sample container may be hot isostatically pressed (HIP) transformation toughened zirconia (TTZ) or partially stabilized zirconia (PSZ), and the outer cover is constructed from high strength engineering materials such as TTZ, PSZ, glass filled PEEK, Macor™, quartz, or other non-RF interfering materials. A length to inner diameter ratio of the sample container may be from 50 to 100. The sample container may be produced from hot isostatically treated transformation toughened zirconia with an OD to ID ratio of less than 5 and greater than 2. The sample container may be mounted to a nonmagnetic base with volume limiting isolation chamber where the sample and pressure source fluids are in pressure communication but not in fluid communication and the volume limited so as to limit contamination of the measurement equipment should the sample container break. The mounting system further may include a piston provided in the channel and configured to apply a pressure to the sample container. The sample container further may comprise a side port. The sample container further may comprise a plug adapted to fit the side port.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing.
In the drawings.

DETAILED DESCRIPTION OF THE INVENTION

Figure 1:
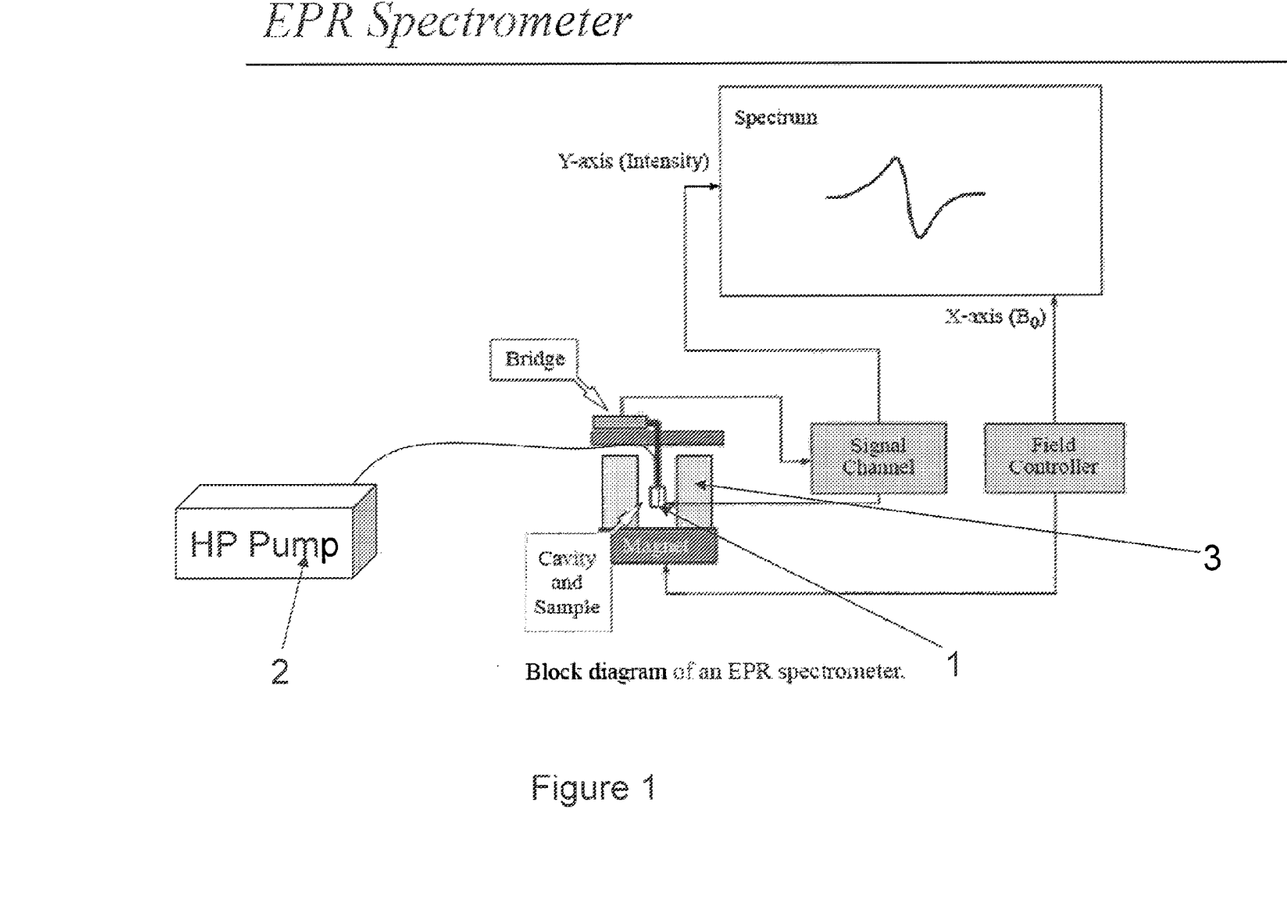
FIG. 1 is a schematic illustration showing a typical EPR system with the high pressure cell and high pressure source. The pressure source is typically an intensifier type device such as the Pressure Biosciences, Inc. HUB440 pressure generator.
Figure 2:
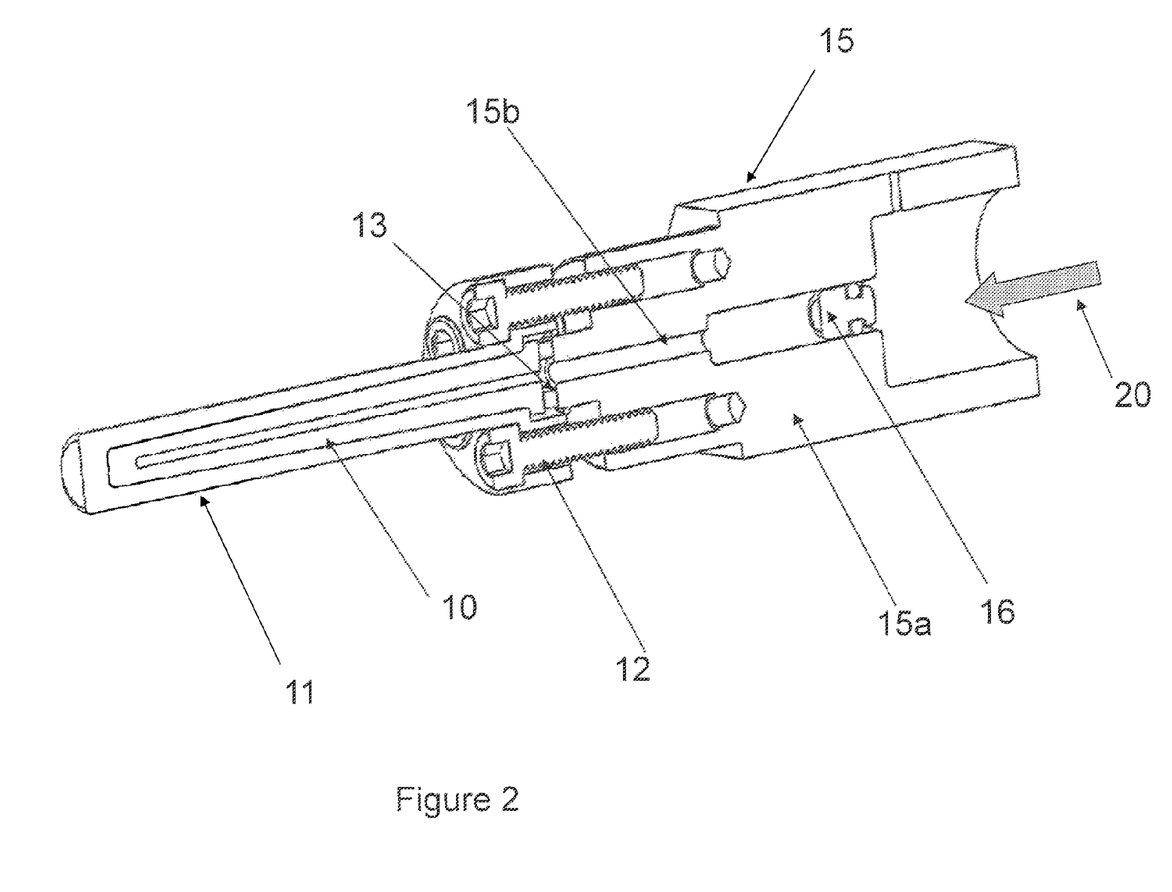
FIG. 2 is a schematic illustration showing a cross section of a complete sample containing system in accordance with one or more embodiments of the invention; wherein a taper angle is used to create a high compressive stress on the sample container.
Figure 3:
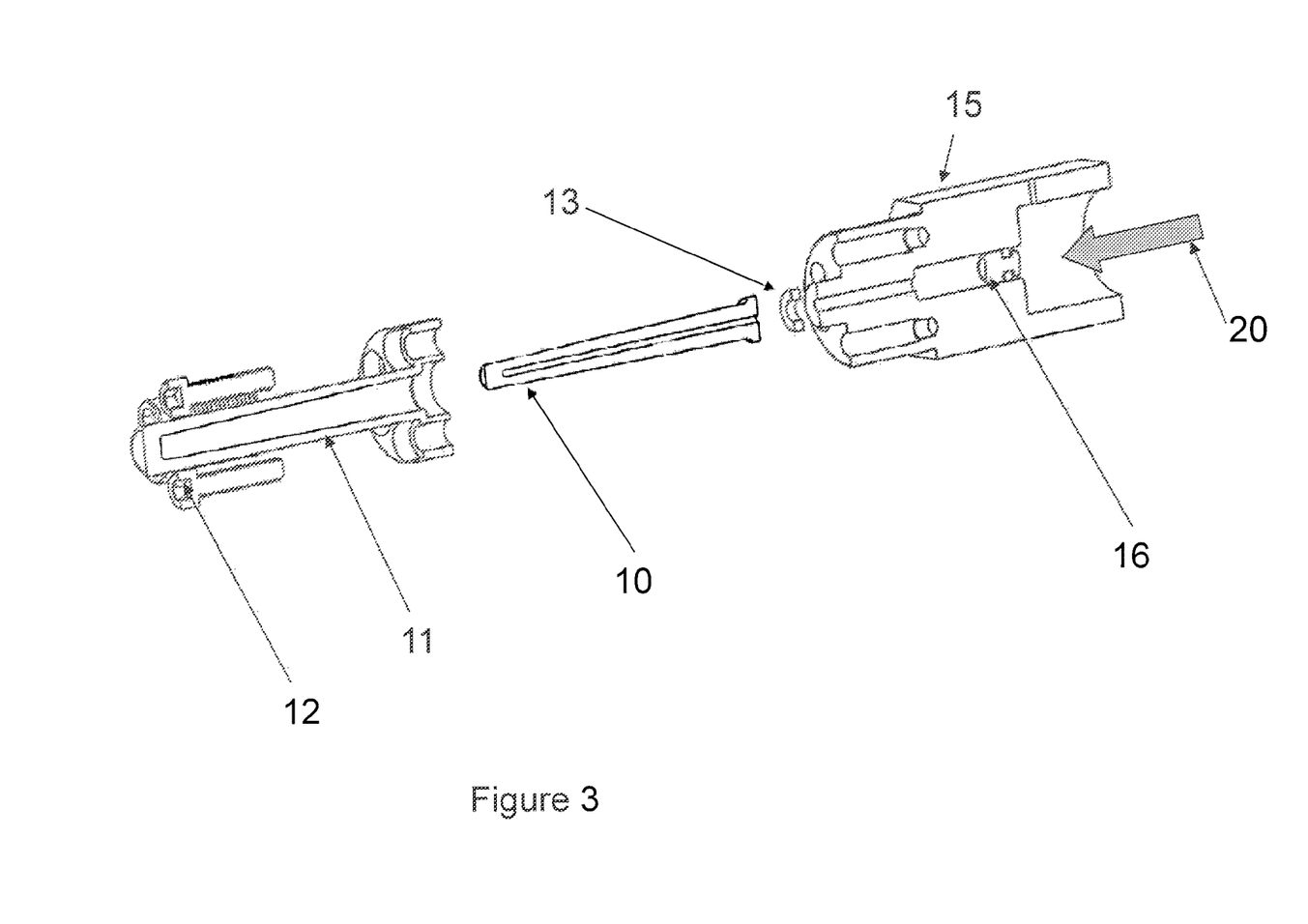
FIG. 3 is an exploded illustration showing the same assembly as FIG. 2.

In accordance with one or more embodiments, the invention relates to a sample containing system comprising a sample containing device 1, mounted inside an EPR or NMR or other system requiring a nonmetallic sample holder 3, and a source of high pressure fluid 2. The sample containing device consists of a sample container 10 having an inner receptacle and an outer cover 11 for the said sample container and a mounting base that puts the sample into pressure communication to a source of high pressure fluid but not in fluid communication. The outer cover 11 is constructed such that it imposes a compressive stress on the sample container 10 by way of a wedging action, a forced interference fit, filament winding, or other means of generating a high compressive stress on the sample container. The mounting base consists of a small defined volume cavity separated by a moving piston which limits the volume of fluid that can enter the measurement device should the sample container fail or otherwise leak. This piston or movable partition will also prevent mixing of the sample with the pressure media. The compressive stress is applied to the sample container by configuring the outside of the sample container and an inside of the outer cover with mating taper angles. The compressive stress may be generated by the use of a press interference fit of the outer cover onto the sample container with or without the use of an initial differential temperature.

Embodiments of the sample containing system may include fabricating the sample container from a suitable non-metallic material capable of being subjected to measurement of magnetically induced RF signals. Specifically, both the sample container and outer cover are constructed from high strength non-metallic materials such as Yttria-stabilized zirconia (YSZ), Glass Reinforced Polyetheretherketone (PEEK), quartz, glass, or other very low or materials that do not significantly interfere with transmission of electromagnetic radiation or magnetic field.

The presence of a high compressive stress created by the cover on the sample container allows the sample container to work at a higher internal pressure than otherwise possible. Without this compressive stress, most ceramic materials could not withstand the tensile stresses generated by a high internal fluid pressure. Tests show that a simple small cylindrical pressure cell, even when constructed from the highest quality ceramic, cannot withstand an internal pressure of greater than 40,000 psi.

In one embodiment of the concept, the sample container and the outer cover both have angular tapers of approximately 1 degree. The angular surface allows the creation of a compressive stress when the outer cover is pulled tightly over the sample container via a number of screws 12 located in the mounting system. In one embodiment of this approach, a force limiting washer 13 can be used to limit the compressive forces generated by the coupling 12 so as to prevent over stressing the either of the two components. This is accomplished by the deformation of the washer 13 should the compressive force becomes too high.

Figure 4:
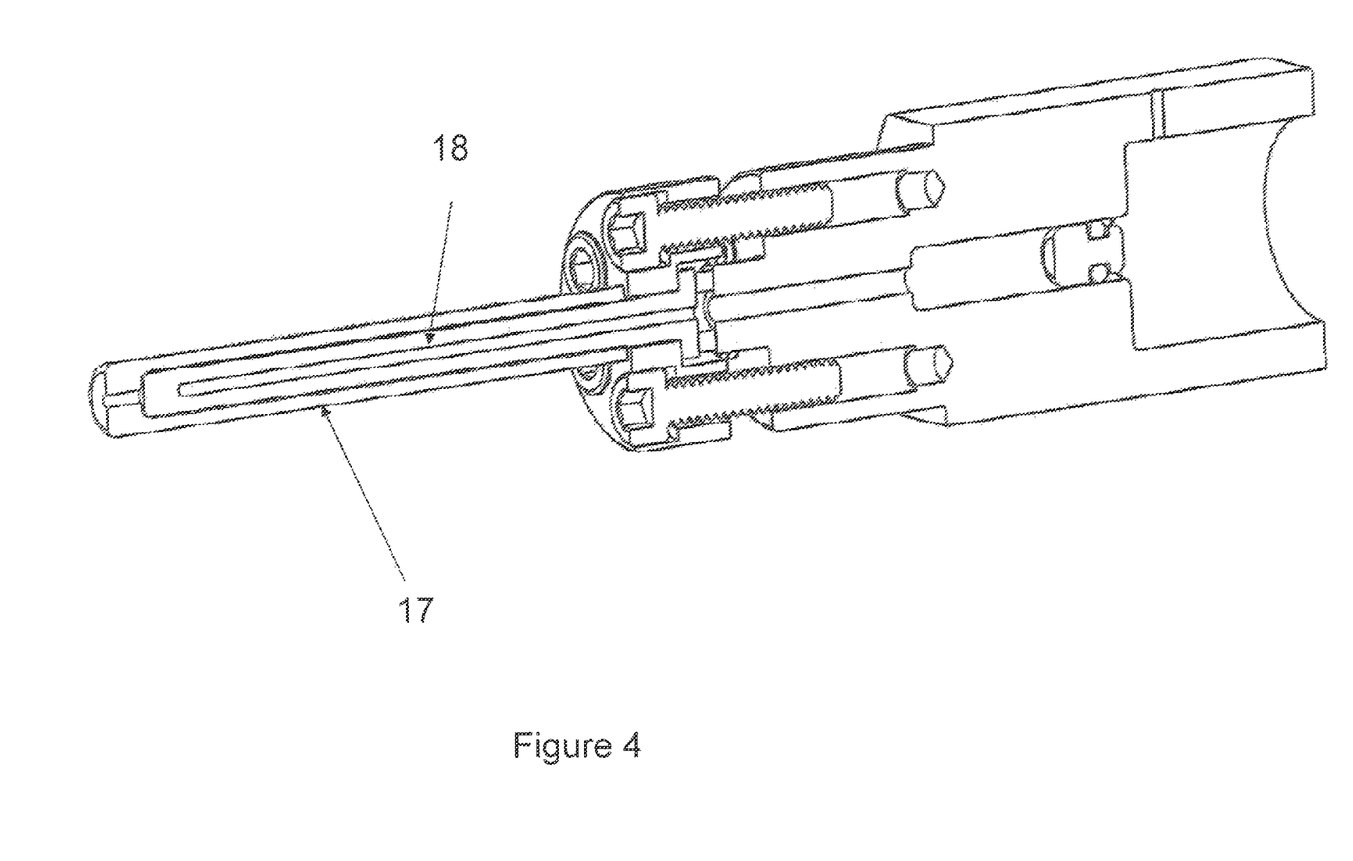
FIG. 4 is a schematic illustration showing an alternative method of creating a high compressive stress in the sample container wherein a press fitted outer cover is used.

In another alternative embodiment of this invention, a simple non-taper outer cover 17 is forced onto the sample container so as to put a non-taper sample container 18 into compressive stress. A small hole is on one end of the outer cover so as to vent the air inside during the pressing process. This interference may be achieved with or without the use a thermal effects. For example, by heating a cover, its diameter can be enlarged so as to facilitate easier press fit.

In a third embodiment of this invention, a thin and flexible glass or fused silica filament is wound with uniform tension around the ceramic cylindrical vessel forming multiple layers covering the entire length of the said vessel. The tension of the filament provides desired compression stress exerted onto the ceramic vessel.

In accordance with one or more embodiments, the invention relates to a mounting system 15 that incorporates a design element which fluidly isolates the sample 10 from the pressurization fluid 20. The mounting system 15 includes a body 15a having centrally located channel 15b formed therein. The design concept typically is constructed as a floating o-ring piston 16 or a movable diaphragm which prevents fluid communication but not pressure communication. In this embodiment of the invention, the volume of the fluid isolating chamber is predetermined such that only the required fluid needed to compress the sample container is present. This is frequently no more than 10 to 20% of the volume of the sample cell due to the low compressibility of most fluids. This small volume prevents the discharge of a large amount of fluid into the analytical measurement instrument should the sample tube break. If the sample container breaks, the piston 16 will move to the end of the isolator volume and only the available volume defined between the sample tube and the isolator piston and no additional flow will be allowed into the measurement equipment. This can significantly reduce the amount of fluid and high pressure energy released into the measurement device to which the sample is connected to or inserted into.

Since electromagnetic waves cannot penetrate metal and metal alloys, the sample container can not be made from such materials. This leaves only polymers, ceramics, and glasses as potential construction materials. Polymers have low yield strength and cannot be use to fabricate pressure vessels of very high pressure (>5,000 psi) capabilities. The highest engineered plastics have a yield-strength typically lower than 30,000 psi.

While ceramics have very high yield strength, they are not capable of withstanding high tensile stresses due to internal defects and the lack of a "ductile" deformation mode. When loaded in tension, small defects within ceramics quickly weaken the ceramic and lead to brittle fracture of the whole pressure vessel. Recently, a small group of ceramics have been developed which use transformation toughening to increase fracture toughness, these are the most crack resistant ceramics. However, even these ceramics are not able to serve as high pressure vessel. As a ceramic object increases in size, the probability of having such a defect increases. Thus, a sample container of increasing size becomes increasing difficult. Testing data shows that even for these high quality materials, the maximum internal pressure that could be tolerated is less than 30,000 psi.

Thus, the approach taught by Wald is not capable of serving a pressure requirement of greater than approximately 35,000 psi.

This present invention illustrates that additional wall thickness does not produce a significant increase in pressure resistance due to the increased chance of having defects and the reduced role of the added material to carry load. In order to increase the ability of the ceramic to resist fracture, internal defects must be minimized. This applications shows that hot isostatic pressed (HIPed) process can be used to increase the density of the sample container. Tests clearly show that HIP increase the pressure resistance of the sample container.

However, even with the selection of high toughness ceramics such as yttria stabilized zirconia (YSZ), processed with defect reducing HIP processing, strength is insufficient for use at pressures above 40 ksi. In order to achieve pressure higher than 40,000 psi, additional design strategies must be utilized. This involves the use of compressive stresses applied to the brittle ceramic tube so as to reduce the tensile stresses within the sample tube. This could be accomplished using an interference fit. The interference can be created by way of a press fit of the wedging action created by fitting two taper surfaces together. Alternatively, this interference fit may be created by using a press fit.

| Test Results | |
|---|---|
| Tube Design | Burst Failure Pressure |
| HIP YSZ (yttria stabilized zirconia ceramic) (2.2LX.031IDX0.118OD) | 27 kis, 28 ksi |
| HIP YSZ (1.6LX.031IDX0.118OD) | 39 ksi |
| ZTA (Toughened alumina; not-HIPed) (2.2LX.031IDX0.118OD) | 18 ksi |
| HIP YSZ 1.0"LX0.028"IDX0.157"OD | 34 ksi, 36 ksi |
| HIP YSZ 1.2"LX0.028"IDX0.157"OD | 35 ksi |
| HIP YSZ (thin wall) (1.6LX0.080IDX0.157OD) | 30 ksi |
| YSZ non-HIPed (1.6LX0.080IDX0.157OD) | 19 ksi |

| AmZirOx 86 Zirconia Properties | | |
|---|---|---|
| Typical Properties | Units | Value |
| Composition | wt % | 95% zirconia, 5% yttria |
| Color | — | Ivory |
| Bulk Density | g/cm$^3$ | 6.01 |
| Water Absorption | % | 0 |
| Gas Permeation | % | 0 |
| Grain Size | Microns | 0.5 |
| Hardness (Vickers) | HV | 1290 |
| Flexural strength | MPa (kpsi) | 1000 (145) |
| Modulus of Elasticity | GPa (psi · 10$^6$) | 204 (30) |
| Fracture Toughness | MPa · m$^{1/2}$ | 7 |
| Poisson's Ratio | — | 0.31 |
| Thermal Expansion (25° C.-1000° C.) | 10$^{-6}$/° C. (10$^{-6}$/° F.) | 10.3 (5.8) |
| Thermal Conductivity | Btu · in/ft$^2$ · h · ° F. | 15 |
| Specific Heat | cal/g-° C. | 0.32 |
| Maximum Temperature Use (no load) | ° C. (° F.) | 2400 (4350) |

Figure 5:
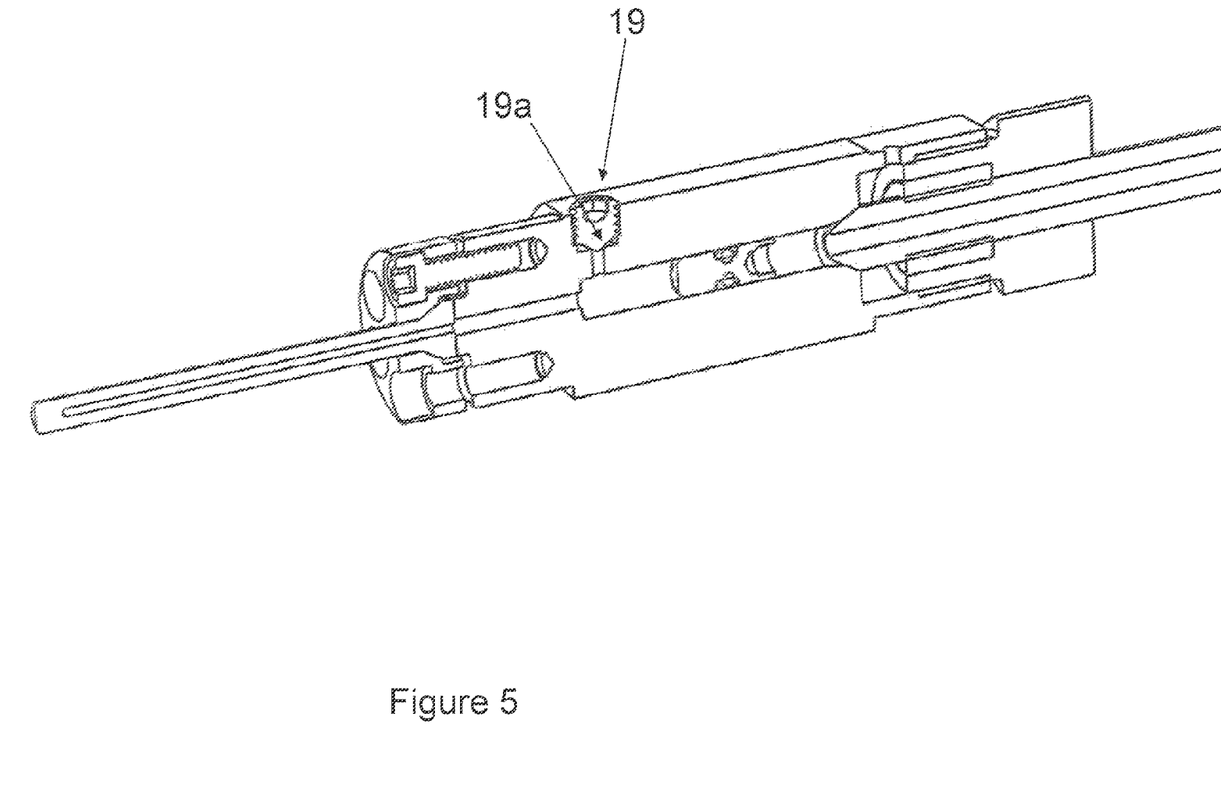
FIG. 5 is a schematic illustration showing a cross section of a complete sample containing system in accordance with one or more embodiments of the invention; wherein a side port into the sample tube and a plug is included into the system.

In certain embodiments, the material used to construct the sample container may be hot isostatically pressed (HIP) transformation toughened zirconia (TTZ) or partially stabilized zirconia (PSZ), and the outer cover is constructed from high strength engineering materials such as TTZ, PSZ, glass filled PEEK, Macor™, quartz, or other non-RF interfering materials. A length to inner diameter ratio of the sample container may be from 50 to 100. The sample container may be produced from hot isostatically treated transformation toughened zirconia with an OD to ID ratio of less than 5 and greater than 2. The sample container may be mounted to a nonmagnetic base with volume limiting isolation chamber where the sample and pressure source fluids are in pressure communication but not in fluid communication and the volume limited so as to limit contamination of the measurement equipment should the sample container break. In accordance with one or more embodiments, also described herein is a side port 19 as provided in FIG. 5. The side port 19 allows filling of samples into the sample tube. In some embodiments, the side port includes a plug 19a (e.g., a removable plug). In some embodiments, the side port includes a threaded removable plug able to withstand the pressure generated within the sample tube. In certain embodiments, in place of the plug 19a, a syringe adaptor can be inserted (e.g., screwed into) the port to allow a syringe to be connected to the port.

Figure 6:
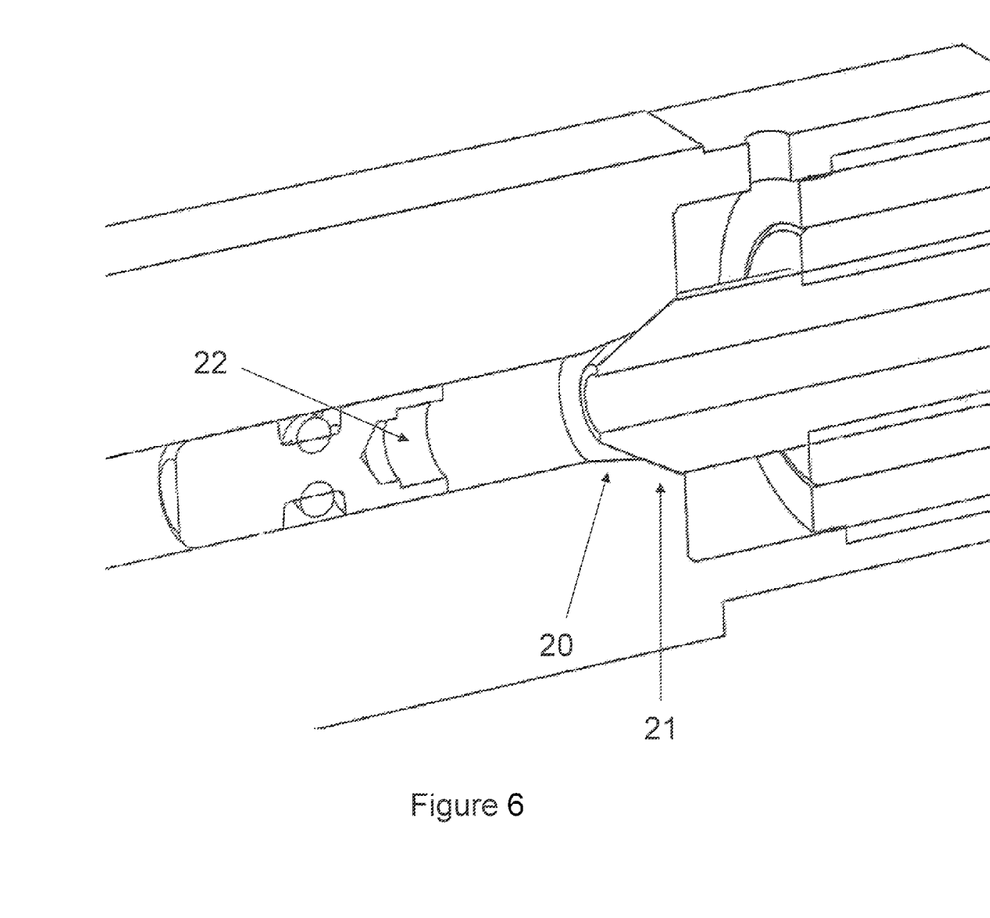
FIG. 6 is an enlarged illustration showing a close-up view of the double taper of the high pressure tube and isolator plug of the sample container.

In accordance with one or more embodiments, a double taper 20 and 21 is used to allow sealing of a high pressure tube. In addition, also described herein is a rear end threaded isolator plug 22. In some embodiments, the isolator plug 22 can be readily removed. In general, with a single taper setup, deforming can occur. This deforming can create a more narrow passage preventing removal of an isolator.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A sample containing system, comprising:
  a non-metallic sample container for measurement of magnetically induced RF signals, the sample container defining an inner sample receptacle configured to hold a sample fluid;
  an outer cover configured to mate with the sample container such that the cover imposes a compressive stress over the sample container thus, in operation, allowing the sample container to reach operating pressures of greater than 30,000 psi that would normally burst the sample container; and
  a mounting system configured to securingly receive the sample container and the outer cover, the mounting system including:
    a body having a channel formed therein, the channel in fluid communication with a source of pressurization fluid; and
    a piston, movable within the channel, configured to pressurize the sample within the inner sample receptacle while fluidly isolating the sample fluid in the inner sample receptacle from the pressurization fluid.

2. The sample containing system of claim 1, wherein the compressive stress is applied to the sample container by configuring the outside of the sample container and an inside of the outer cover with mating taper angles.

3. The sample containing system of claim 2, further comprising screw fasteners configured to secure the outer cover to the mounting system.

4. The sample containing system of claim 1, wherein the compressive stress is generated by the use of a press interference fit of the outer cover onto the sample container with or without the use of an initial differential temperature.

5. The sample containing system of claim 1, wherein the material used to construct the sample container is hot isostatically pressed (HIP) transformation toughened zirconia (TTZ) or partially stabilized zirconia (PSZ), and the outer cover is constructed from high strength engineering materials such as TTZ, PSZ, glass filled PEEK, Macor™, quartz, or other non-RF interfering materials.

6. The sample containing system of claim 5, wherein a length to inner diameter ratio of the sample container is from 20 to 100.

7. The sample containing system of claim 1, wherein the sample container is produced from hot isostatically treated transformation toughened zirconia with an OD to ID ratio of less than 5 and greater than 2.

8. The sample containing system of claim 1, wherein the sample container is mounted to a nonmagnetic base with volume limiting isolation chamber where the sample and pressure source fluids are in pressure communication but not in fluid communication and the volume limited so as to limit contamination of the measurement equipment should the sample container break.

9. The sample containing system of claim 1, wherein the sample container further comprises a side port.

10. The sample containing system of claim 9, wherein the sample container further comprises a plug adapted to fit the side port.

11. The sample containing system of claim 1, wherein the operating pressure is greater than 40,000 psi.

* * * * *